(12) United States Patent
Saxton, Jr. et al.

(10) Patent No.: US 9,206,091 B2
(45) Date of Patent: Dec. 8, 2015

(54) PROCESSES AND SYSTEMS FOR SYNTHESIS GAS CONVERSION USING A HYBRID FISCHER-TROPSCH CATALYST IN A COMPACT HEAT EXCHANGE REACTOR

(71) Applicants: Robert James Saxton, Jr., Pleasanton, CA (US); Kandaswamy Jothimurugesan, Hercules, CA (US); Charles Leonard Kibby, Benicia, CA (US)

(72) Inventors: Robert James Saxton, Jr., Pleasanton, CA (US); Kandaswamy Jothimurugesan, Hercules, CA (US); Charles Leonard Kibby, Benicia, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 104 days.

(21) Appl. No.: 14/219,774

(22) Filed: Mar. 19, 2014

(65) Prior Publication Data
US 2014/0343175 A1 Nov. 20, 2014

Related U.S. Application Data

(60) Provisional application No. 61/823,076, filed on May 14, 2013.

(51) Int. Cl.

| | | |
|---|---|---|
| C07C 27/00 | (2006.01) | |
| C07C 1/04 | (2006.01) | |
| B01J 19/00 | (2006.01) | |
| B01J 35/00 | (2006.01) | |
| B01J 8/00 | (2006.01) | |
| B01J 23/75 | (2006.01) | |
| B01J 23/89 | (2006.01) | |
| B01J 29/00 | (2006.01) | |
| B01J 35/02 | (2006.01) | |
| B01J 35/10 | (2006.01) | |
| C10G 2/00 | (2006.01) | |
| F28F 3/00 | (2006.01) | |
| F28D 9/00 | (2006.01) | |

(52) U.S. Cl.
CPC .............. *C07C 1/0435* (2013.01); *B01J 8/008* (2013.01); *B01J 19/00* (2013.01); *B01J 19/0093* (2013.01); *B01J 23/75* (2013.01); *B01J 23/8913* (2013.01); *B01J 29/00* (2013.01); *B01J 35/0006* (2013.01); *B01J 35/023* (2013.01); *B01J 35/1019* (2013.01); *C07C 1/042* (2013.01); *C10G 2/334* (2013.01); *F28D 9/00* (2013.01); *F28F 3/00* (2013.01); *B01J 2208/00026* (2013.01); *B01J 2219/00049* (2013.01); *B01J 2219/00761* (2013.01); *B01J 2219/00783* (2013.01); *B01J 2219/00822* (2013.01); *B01J 2219/00826* (2013.01); *B01J 2219/00835* (2013.01); *B01J 2219/00873* (2013.01)

(58) Field of Classification Search
CPC . C10G 2/334; C10G 2/32; B01J 2219/00049; B01J 2208/00026; B01J 2219/00835; C07C 1/0435; C07C 1/042
USPC ......................................... 518/700, 712, 715
See application file for complete search history.

(56) References Cited

U.S. PATENT DOCUMENTS

| | | |
|---|---|---|
| 8,100,996 B2 | 1/2012 | Simmons et al. |
| 8,203,023 B2 | 6/2012 | Wang et al. |
| 2013/0041050 A1 | 2/2013 | Luzenski et al. |

FOREIGN PATENT DOCUMENTS

WO  WO 2012107718  8/2012

*Primary Examiner* — Jafar Parsa
(74) *Attorney, Agent, or Firm* — Karen R. DiDomenicis (57) ABSTRACT

Disclosed are a process and a system for synthesis gas conversion. The process includes contacting a synthesis gas feed of hydrogen and carbon monoxide having a $H_2/CO$ ratio from 0.5 to 3.0 with a hybrid catalyst of particles having a particle size from 50 to 500 μm and having at least one zeolite and a Fischer-Tropsch component wherein the ratio of zeolite to Fischer-Tropsch component is from 0.1:1 to 30:1 and the hybrid catalyst includes from 0.5 to 40 wt % Fischer-Tropsch component. The process is conducted in a compact heat exchange reactor having a set of reaction passages disposed between a synthesis gas feed header and a products header and a set of coolant passages disposed between a coolant inlet header and a coolant outlet header. The set of coolant passages conducts a coolant therethrough, and the set of reaction passages contains the hybrid catalyst therein and conducts synthesis gas and reaction products therethrough. The process is conducted at a temperature from 200 to 2800° C., a pressure from 5 to 40 atmospheres, a recycle ratio from 1 to 3, and a gaseous hourly space velocity less than 20,000 volumes of gas per volume of catalyst per hour. The effluent produced includes a hydrocarbon product containing at least 50 wt % $C_{5+}$ hydrocarbons and less than 5 wt % $C_{21+}$ hydrocarbons at a $C_{5+}$ productivity from 0.05 to 2 $g_{C5+}/g_{cat}/h$.

15 Claims, 3 Drawing Sheets

PROCESSES AND SYSTEMS FOR SYNTHESIS GAS CONVERSION USING A HYBRID FISCHER-TROPSCH CATALYST IN A COMPACT HEAT EXCHANGE REACTOR

CROSS-REFERENCE TO RELATED APPLICATIONS

This application claims the benefit of U.S. Provisional Application No. 61/823,076, filed May 14, 2013.

FIELD

The present disclosure relates to processes and systems for synthesis gas conversion using hybrid Fischer-Tropsch catalysts containing a Fischer-Tropsch component and a zeolite component in a compact heat exchange reactor to produce liquid hydrocarbon fuels.

BACKGROUND

Monetizing natural gas associated with remote oil production or stranded gas reserves having no access to distribution infrastructure presents enormous challenges. Flaring or venting of such "associated gas" is both wasteful and detrimental to the environment. It is often more desirable to convert the natural gas into higher molecular weight hydrocarbons at a remote location near the source than to transport the natural gas to another location for conversion.

Many processes, such as Fischer-Tropsch synthesis, can convert methane-derived synthesis gas, also referred to as syngas, to hydrocarbons having a higher molecular weight, e.g., in the wax range. Fischer-Tropsch synthesis involves a polymerization reaction beginning with a methylene intermediate to produce a wide distribution of hydrocarbons ranging from light gases to solid wax. The resulting higher molecular weight hydrocarbons are difficult to transport because they are solid at room temperature.

Since it is desirable to transport waxy petroleum crude and Fischer-Tropsch products from remote sites to distant commercial refineries, there have been attempts to develop acceptable approaches for this transportation. For instance, waxy crude oils are shipped in specially equipped crude carriers at temperatures up to around 160° F. (71° C.). Typical maximum temperatures for conventional crude carriers are 140° F. (60° C.). The use of conventional crude carriers, those that ship materials at temperatures at or below 140° F., is preferred whenever possible because these carriers have significantly lower operating costs. Transporting solids requires forming, loading, and unloading facilities and is thus difficult and expensive.

In order to economically monetize remote associated natural gas or stranded gas, it would be desirable to have a way to produce a Fischer-Tropsch product which is blendable with crude oil in a compact, modular unit capable of being placed on offshore production structures. Specifically, it would be desirable to produce a hydrocarbon product containing at least 50 wt % $C_{5+}$ and less than 25 wt % $C_{21+}$ hydrocarbons which is a pourable liquid and blendable with crude oil at room temperature at a $C_{5+}$ productivity from 0.05 to 2 $gC_{5+}/gcat/h$.

SUMMARY

In one aspect, a process for synthesis gas conversion is provided. The process includes contacting a synthesis gas feed of hydrogen and carbon monoxide having a $H_2/CO$ ratio from 0.5 to 3.0 with a hybrid catalyst of particles having a particle size from 50 to 500 μm and having at least one zeolite and a Fischer-Tropsch component wherein the ratio of zeolite to Fischer-Tropsch component is from 0.1:1 to 30:1 and the hybrid catalyst includes from 0.5 to 40 wt % Fischer-Tropsch component. The process is conducted in a compact heat exchange reactor having a set of reaction passages disposed between a synthesis gas feed header and a products header and a set of coolant passages disposed between a coolant inlet header and a coolant outlet header. The set of coolant passages conducts a coolant therethrough, and the set of reaction passages contains the hybrid catalyst therein and conducts synthesis gas and reaction products therethrough. The process is conducted at a temperature from 200° C. to 280° C., a pressure from 5 to 40 atmospheres, a recycle ratio from 1 to 3, and a gaseous hourly space velocity less than 20,000 volumes of gas per volume of catalyst per hour. The effluent produced includes a hydrocarbon product containing at least 50 wt % $C_{5+}$ hydrocarbons and less than 5 wt % $C_{21+}$ hydrocarbons at a $C_{5+}$ productivity from 0.05 to 2 $g_{C5+}/g_{cat}/h$.

In another aspect, a system for synthesis gas conversion is provided. The system includes a hybrid catalyst of particles having a particle size from 50 to 500 μm and including at least one zeolite and a Fischer-Tropsch component wherein the ratio of zeolite to Fischer-Tropsch component is from 0.1:1 to 30:1 and the hybrid catalyst includes from 0.5 to 40 wt % Fischer-Tropsch component. The hybrid catalyst is contained in the reaction passages of a compact heat exchange reactor having a set of reaction passages disposed between a synthesis gas feed header and a products header and a set of coolant passages disposed between a coolant inlet header and a coolant outlet header.

DESCRIPTION OF THE DRAWINGS

These and other objects, features and advantages of the present invention will become better understood with reference to the following description, appended claims and accompanying drawings where:

DETAILED DESCRIPTION

Compact Heat Exchange Reactor

Compact heat exchange reactors as used in the presently disclosed processes and systems are of the type derived from compact heat exchangers, particularly of the plate heat exchanger type and the plate-fin heat exchanger type. Compact heat exchange reactors are also referred to as microchannel reactors and mini-channel reactors. Compact heat exchange reactors suitable for use in the processes and systems of the present disclosure include alternating chambers, channels or passages arranged adjacent to one another so that heat is transferred between fluids in adjacent passages. The passages can be straight or they may include curvature and/or changes of direction. The passages can have any of a variety of cross-sectional shapes, including rectangular, square, circular, oval, triangular, etc. The passages can be defined by assemblies of thin plates, or by assemblies of thin plates which include fins between the thin plates. The fins can transfer heat and contribute to the structural integrity of the heat exchanger.

Such heat exchangers are known to have a high heat transfer surface area to volume ratio, even as high as 10,000 $m^2/m^3$. Compact heat exchange reactors can advantageously utilize this high surface area density to provide enhanced heat removal from exothermic reactions such as Fischer-Tropsch reactions.

Suitable compact heat exchange reactors for use in the present disclosure include at least a first set of passages and a second set of passages which are arranged so that the first set of passages and the second set of passages are adjacent to each other so that heat can be transferred between the first set of passages and the second set of passages. The passages within each of the first and second sets of passages run parallel to one another. Fluids flowing within the first set of passages and the second set of passages are not themselves in fluid communication with one another. The first set of passages is in fluid communication with a first inlet header and a first outlet footer, and the second set of passages is in fluid communication with a second inlet header and a second outlet footer. The first set of passages and the second set of passages can be arranged such that fluids flowing within the first set of passages and the second set of passages may be flowing in the same direction (parallel flow), in opposite directions (counterflow) or cross directions (crossflow).

In the processes and systems of the present disclosure, at least one set of passages, also referred to herein as the reaction passages, contains the hybrid catalyst. The hybrid catalyst, in either an integral particle form or a mixed particle form, to be described further herein, can be included within the reaction passages. This can be done in any of several known ways, including but not limited to, (1) coating at least a portion of the inner walls, or fins if present, of the reaction passages with a coating including hybrid catalyst particles, e.g., by any known convenient spraying, washcoating, dip coating or electroless plating technique, (2) at least partially filling the reaction passages with hybrid catalyst particles, and/or (3) inserting a removable insert, e.g., a honeycomb structure or a microfibrous mesh, including hybrid catalyst particles on the surface thereof into the reaction passages.

Synthesis gas (also referred to as syngas) feed and treatment gas feeds such as hydrogen are provided to the reaction passages through a syngas feed header. Through the reaction passages, the syngas is conducted such that the syngas contacts the hybrid catalyst and reaction products are formed. The reaction passages can have surface features and/or capillary features as is known in the compact heat exchanger art. Surface features disrupt or modify flow within the passages as is known in the compact heat exchanger art. Capillary features increase the depth of catalyst material coated thereon. The reaction products flow through the reaction passages and collect in a footer downstream of the reaction passages, also referred to as the products footer. The effluent including the hydrocarbon products of the reaction is removed from the products footer. The reaction passages connect to the syngas feed header and the products footer. The syngas feed header and the products footer are integral to the reactor. As is known, a retainer can be included at the downstream end of the reaction passages to prevent particles from exiting the reaction passages.

Through at least one other set of passages, also referred to herein as coolant passages, a coolant, also referred to as a heat exchange fluid, is conducted. During Fischer-Tropsch reactions, the heat exchange fluid absorbs heat from an adjacent reaction passage or a reaction passage in thermal contact. Passages are adjacent when separated by a wall. Passages are in thermal contact when they exchange heat with each other.

The coolant entering the coolant passages can be at a temperature from 100° C. to 300° C., and in one embodiment 200° C. to 250° C. The coolant exiting the coolant passages may be at a temperature in the range of 150° C. to 300° C., and in one embodiment 200° C. to 250° C. During Fischer-Tropsch reactions, the outlet coolant temperature cannot be greater than the reaction temperature, which is limited to 250° C. when cobalt is used as the Fischer-Tropsch catalyst component.

While the heat exchange fluid is referred to as a "coolant" herein, it should be noted that for catalyst activation and regeneration, the heat exchange fluid is externally heated and used as a heating medium to heat the reaction passages during activation, such that a temperature up to 350° C. for fresh Co catalysts and 250° C. for once reduced and reoxidized Co catalysts is needed.

The residence time of the heat exchange fluid in the heat exchange channels may range from about 1 to about 2000 ms, and in one embodiment about 10 to about 500 ms. The pressure drop for the heat exchange fluid as it flows through the heat exchange channels may range up to about 10 atm/m, and in one embodiment from about 1 to about 10 atm/m, and in one embodiment from about 2 to about 5 atm/m. The heat exchange fluid may be in the form of a vapor, a liquid, or a mixture of vapor and liquid.

For cooling, in a preferred embodiment, the coolant is water because of its high heat of vaporization to form steam. The steam is generated by the heat of the Fischer-Tropsch reaction from the adjacent reaction passages. In alternative embodiments, the coolant can be any heat exchange medium suitable for cooling a Fischer-Tropsch reaction including but not limited to air, gaseous nitrogen, inert gases, carbon monoxide, oils such as mineral oil, and heat exchange fluids such as Dowtherm A and Therminol which are available from The Dow Chemical Company (Midland, Mich.). For heating, similar heat exchange media may be used, except that the heat of vaporization is not required and gases may be preferred.

The total rate of heat transfer between the fluids flowing in the reaction passages and the coolant passages can be expressed as $Q=UA\Delta T_m$ where U is the overall heat transfer coefficient, A is the total surface area of the heat transfer, and $\Delta T_m$ is the absolute temperature difference between the fluids.

The coolant may undergo a partial or full phase change as it flows in the coolant passages. This phase change may provide additional heat removal from the reaction passages beyond that provided by convective cooling. For a liquid coolant being vaporized, the additional heat being transferred from the reaction passages may result from the latent heat of vaporization required.

The pressure within each individual coolant passages may be controlled using obstructions, orifices and/or mechanisms upstream of or in the coolant passages. By controlling the pressure within the coolant passages, the temperature within the coolant passages and thus the temperature in the reaction passages adjacent to or in thermal contact with the coolant passages can be controlled. This provides the ability to control the temperature of each reaction passage.

The coolant passages are positioned and connected between a coolant inlet header and a coolant outlet footer. The coolant is provided to the reactor at one end of the coolant passages through the coolant inlet header. At the other end of the coolant passages, the coolant can be removed from the coolant outlet footer. The coolant inlet header and the coolant outlet footer are integral to the reactor.

In one embodiment, the passages in the compact heat exchange reactor are formed from any material that provides sufficient strength, dimensional stability and heat transfer characteristics to permit operation of the desired process. These materials may include aluminum; titanium; nickel; copper; chromium; alloys of any of the foregoing metals; brass; steel (e.g., stainless steel); quartz; silicon; or a combination of two or more thereof. Each microchannel reactor may be constructed of stainless steel with one or more copper or aluminum waveforms being used for forming the channels. The passages in the compact heat exchange reactor can be formed from thermally conductive metallic materials, e.g., aluminum, copper, stainless steel, and cobalt or iron alloys and mixtures thereof. In one embodiment, the passages in the compact heat exchange reactor are formed from ceramic materials.

In one embodiment, the reaction passages and the coolant passages may have at least one dimension (measured from wall-to-wall, not including the catalyst thickness) of 1.0 cm or less, preferably 2.0 mm or less, even about 1.0 mm or less, depending on the arrangement of the catalyst (e.g., coated on the walls, present as particles or monolithic inserts, etc.) and the lengths of the passage. For longer passages and for particulate or monolithic inserts, the passages must be wide enough to allow easy filling and removal of the passages with catalyst and to avoid excessive pressure drops. Short passages with thin coatings of catalyst can be as narrow as 1 mm. The height and/or width of a reaction passage is preferably about 2 mm or less. The length of a reaction passage is typically longer. Preferably, the length of a reaction passage is greater than 1 cm, even greater than 20 cm, even greater than 50 cm, and even greater than 100 cm. The coolant passages may be microchannels or they may have larger dimensions that would classify them as not being microchannels.

In one embodiment, the reaction passages and the coolant passages have a hydraulic diameter of less than 6 mm, even less than 5 mm, and even less than 4 mm. Hydraulic diameter is defined as $(4*A)/P$ where A is the cross sectional area and P is the wetted perimeter of the cross-section. In the case of a round passage, the hydraulic diameter is the diameter of the passage. In the case of a rectangular passage completely filled with fluid, the hydraulic diameter is $2LW/(L+W)$ where L is the length and W is the width of the rectangular cross-section. In the case of a rectangular passage partially filled with fluid, the hydraulic diameter is $4LW/(L+2W)$.

The term "bulk flow path" refers to an open path (contiguous bulk flow region) within the reaction passages or coolant passages. A contiguous bulk flow region allows rapid fluid flow through the passages without large pressure drops. In one embodiment, the flow of fluid in the bulk flow region is laminar. Bulk flow regions within each reaction passage or coolant passage may have a cross-sectional area of about 0.05 to about 10,000 mm$^2$, and in one embodiment about 0.05 to about 5000 mm$^2$, and in one embodiment about 0.1 to about 2500 mm$^2$. The bulk flow regions may comprise from about 5% to about 95%, and in one embodiment about 30% to about 80% of the cross-section of the reaction or coolant passages.

The compact heat exchange reactor may contain, for example, 2, 10, 100, 1000 or more passages.

Tailored heat exchange profiles may be provided with each of these embodiments by controlling the number of coolant passages in thermal contact with the reaction passages. For example, more coolant passages may be provided at or near the entrances to the reaction passages, where reactant pressures and hence, synthesis rates are highest, as compared to downstream parts of the reaction passages, where the opposite is true. The heat exchange profile may be tailored by controlling the flow rate of coolant in the coolant passages. For example, a relatively high rate of flow in the coolant passages in thermal contact with the entrances to the reaction passages may be used in combination with relatively low rates of flow in coolant passages in thermal contact with downstream sections of the reaction passages.

Figure 1:
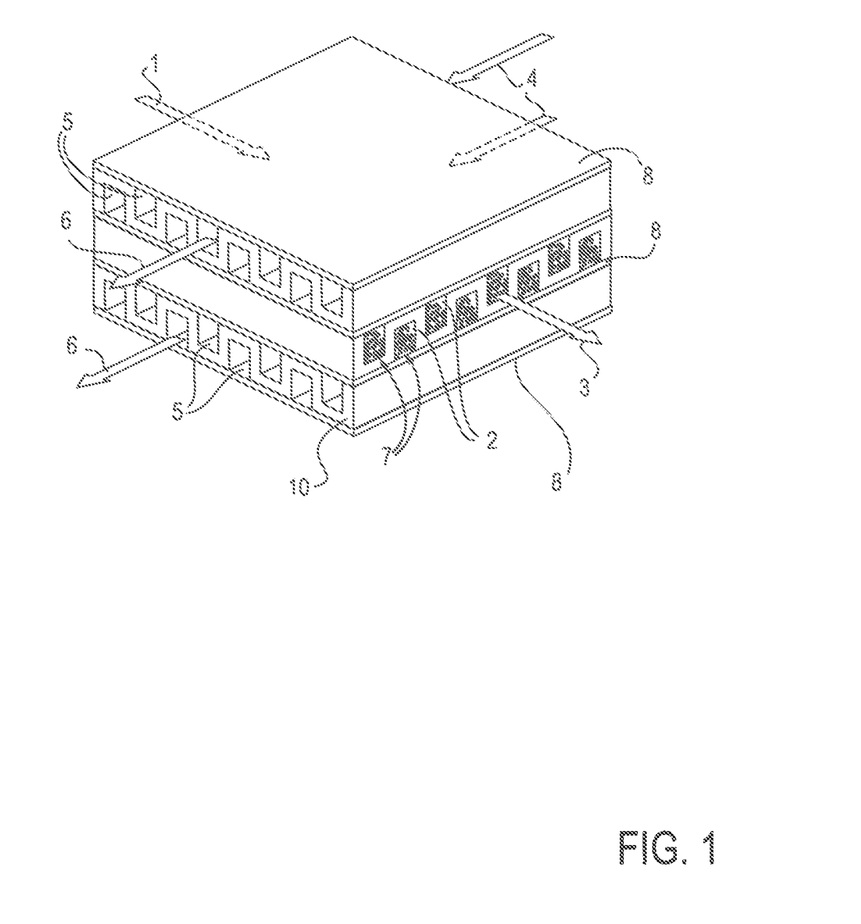
FIG. 1 is a simplified view of one embodiment of a compact heat exchange reactor according to one exemplary embodiment.

FIG. 1 is a simplified view of one embodiment of a compact heat exchange reactor. Syngas feed 1 passes through reaction passages 2 loaded with catalyst 7, such that resulting products 3 exit reaction passages 2. Coolant 4 (in a cross-flow arrangement) flows through adjacent coolant passages 5, and exits the coolant passages 5 as coolant 6. In this embodiment, the reaction passages 2 and coolant passages 5 are formed of corrugated metal sheets 10 positioned between optional metal sheets 8. Reaction products 3 flow downstream from the reaction passages.

In some embodiments, the compact heat exchange reactor is compact and portable. In some embodiments, the compact heat exchange reactor can be placed on offshore floating production structures.

Hybrid Catalyst

According to some embodiments, a hybrid Fischer-Tropsch catalyst, also referred to interchangeably as a hybrid catalyst, is provided which includes at least one synthesis gas conversion component, also referred to as a Fischer-Tropsch component, and at least one zeolite component.

The hybrid catalyst includes at least one zeolite and at least one Fischer-Tropsch component. Preferably, the Fischer-Tropsch component is cobalt. When cobalt is used, the ratio of zeolite to Fischer-Tropsch component can be from 1:1 to 15:1. The Fischer-Tropsch component can be from 5 to 40 wt %, even from 15 to 30 wt %, of the hybrid catalyst.

Throughout the present disclosure, the syngas conversion or Fischer-Tropsch component of the catalyst includes a Group VIII of the Periodic Table metal component, preferably cobalt. References to the Periodic Table and groups thereof used herein refer to the IUPAC version of the Periodic Table of Elements described in the 68th Edition of the Handbook of Chemistry and Physics (CPC Press). The catalyst further includes a catalyst carrier or support. The catalyst carrier is preferably porous, such as a porous inorganic refractory oxide, preferably alumina, silica, titania, zirconia or combinations thereof. The optimum amount of catalytically active metal present on the carrier depends inter alia on the specific catalytically active metal.

The catalytically active Fischer-Tropsch component may be present in the catalyst together with one or more metal promoters or co-catalysts. The promoters may be present as metals or as metal oxide, depending upon the particular promoter concerned. Suitable promoters include metals or oxides of metals from Groups IA, IB, IVB, VB, VIIB and/or VIIB of the Periodic Table, lanthanides and/or the actinides or oxides of the lanthanides and/or the actinides. As an alternative or in addition to the metal oxide promoter, the catalyst may comprise a metal promoter selected from Groups VIIB and/or VIII of the Periodic Table.

The acidic component of the catalyst can be an acid catalyst material such as amorphous silica-alumina or tungstated zirconia or a zeolitic or non-zeolitic crystalline molecular sieve. Examples of suitable molecular sieves include zeolite Y, zeolite X and the so called "ultra stable zeolite Y" and high structural silica:alumina ratio zeolite Y such as for example described in U.S. Pat. Nos. 4,401,556, 4,820,402 and 5,059,567, herein incorporated by reference. Small crystal size zeolite Y, such as described in U.S. Pat. No. 5,073,530, herein incorporated by reference, can also be used. Other zeolites which show utility include those designated as SSZ-13, SSZ- 32, SSZ-32x, SSZ-33, SSZ-46, SSZ-53, SSZ-55, SSZ-57, SSZ-58, SSZ-59, SSZ-64, ZSM-5, ZSM-11, ZSM-12, ZSM-23, H-Y, beta, mordenite, SSZ-74, ZSM-48, TON type zeolites, ferrierite, SSZ-60 and SSZ-70. Non-zeolitic molecular sieves which can be used include, for example silicoaluminophosphates (SAPO), ferroaluminophosphate, titanium aluminophosphate and the various ELAPO molecular sieves described in U.S. Pat. No. 4,913,799 and the references cited therein. Details regarding the preparation of various non-zeolite molecular sieves can be found in U.S. Pat. No. 5,114,563 (SAPO); U.S. Pat. No. 4,913,799 and the various references cited in U.S. Pat. No. 4,913,799, hereby incorporated by reference in their entirety. Mesoporous molecular sieves can also be included, for example the M41S family of materials (J. Am. Chem. Soc. 1992, 114, 10834-10843), MCM-41 (U.S. Pat. Nos. 5,246,689, 5,198,203, 5,334,368), and MCM48 (Kresge et al., Nature 359 (1992) 710).

The amount of acidic component used in the catalyst can be suitably varied to obtain the desired product. For instance, if the amount of acidic component is too low, there may be insufficient cracking to remove a desired amount of wax; whereas if too much acidic component is used, there may be excessive cracking and the resulting product may be lighter than desired. Also, extreme dilution of the Fischer-Tropsch component lowers the volumetric productivity of the catalyst.

In one embodiment, the hybrid catalyst utilized in the present processes and systems includes particles in the form of particulate solids (e.g., pellets, powder, fibers, and the like) having a particle size from 50 to 500 µm, even from 75 to 300 µm. The hybrid catalyst may have any size and geometric configuration that fits within the reaction passages.

In one embodiment, the hybrid catalyst particles can be in the form of a support containing at least one zeolite and a Fischer-Tropsch component deposited on the support. This is also referred to as the "integral particle form." Hybrid catalysts according to this embodiment are described in U.S. Pat. Pub. No. 2010/0160464, U.S. Pat. No. 7,943,674 and U.S. Pat. Pub. No. 2011/0306686. Alternatively, the catalyst components can be combined in a mixture of discrete particles, each particle containing either the synthesis gas conversion component or the acidic component. In this case, the particle sizes must be small enough so that the two catalytic functions can influence one another (ca. 50-75 µm). In one embodiment, integral hybrid Fischer-Tropsch catalyst extrudate particles are prepared and then pulverized to a desired particle size, e.g. from about 20 to about 50 µm, and the pulverized catalyst particles are then combined with a liquid medium to form a slurry which is then washcoated on the walls of the reaction passages. The preparation of integral, hybrid Fischer-Tropsch catalyst extrudate particles is known from the disclosure of U.S. Patent Publication No. 2010/0160464 A1, herein incorporated by reference in its entirety.

The Fischer-Tropsch catalyst may be made using multiple impregnation steps. For the cobalt catalyst the amount of cobalt can be up to about 45 weight % Co. Initially, the zeolite support can be treated by oxidative calcination at a temperature in the range of from 450° to 900° C., for example, from 600° to 750° C. to remove water and any organics from the zeolite support and to dehydroxylate it. The calcined zeolite support is then impregnated in a dehydrated state with the solution of the metal salts. The calcined zeolite support should not be unduly exposed to atmospheric humidity so as to become rehydrated.

Any suitable impregnation technique can be employed including techniques well known to those skilled in the art so as to distend the catalytic metals in a uniform thin layer on the catalyst zeolite support. For example, the cobalt along with the oxide promoter can be deposited on the zeolite support material by the "incipient wetness" technique. Such technique is well known and requires that the volume of substantially non-aqueous solution be predetermined so as to provide the minimum volume which will just wet the entire surface of the zeolite support, with no excess liquid. Alternatively, the excess solution technique can be utilized if desired. If the excess solution technique is utilized, then the excess solvent present, e.g. acetone, is merely removed by evaporation.

The impregnated catalyst is slowly dried at a temperature of from 110° to 120° C. for a period of about 1 hour so as to spread the metals over the entire zeolite support. The drying step is conducted at a very slow rate in air. The dried catalyst is calcined by heating in flowing air, for example 10 cc/gram/minute, to a temperature in the range of from 200° to 350° C., for example, from 200° to 300° C., that is sufficient to decompose the metal salts and fix the metals. The aforesaid drying and calcination steps can be done separately or can be combined. However, calcination should be conducted by using a slow heating rate of, for example, 0.5° to 3° C. per minute or from 0.5° to 1° C. per minute and the catalyst should be held at the maximum temperature for a period of 1 to 20 hours, for example, for about 2 hours.

The foregoing impregnation steps are repeated with additional solutions in order to obtain the desired metal loading. Platinum and other promoter metal oxides are conveniently added together with cobalt, but they may be added in other impregnation steps, separately or in combination, either before, after, or between impregnations of cobalt.

In an alternative embodiment, the hybrid catalyst particles can be in the form of an intimate mixture of at least one zeolite and a Fischer-Tropsch component. This is also referred to as the "mixed particle form." Hybrid catalysts according to this embodiment are described in U.S. Pat. No. 7,825,164 and U.S. Pat. Pub. No. 2012/0129960.

In an alternative embodiment, the hybrid catalyst can be in the form of one or more layers of a Fischer-Tropsch component and at least one zeolite deposited on the inner walls of reaction passages in a compact heat exchange reactor. The Fischer-Tropsch component and the zeolite can be present in the same catalyst layer(s) or in separate catalyst layers. The average thickness of a catalyst layer measured perpendicular to the wall of a reaction passage is at least 100 µm. In one embodiment, the width and/or height of a reaction passage is 2 mm with a catalyst layer on opposing walls of 0.5 mm.

The catalyst layer can contain between about 10 and about 100 mg, even between about 10 and about 30 mg, of cobalt per gram of support, depending on the dimensions of the reaction passages. The catalyst components can be combined as separate, discrete particles of synthesis gas conversion component and acidic component in a slurry including a liquid medium which is then deposited or coated onto the walls of the reaction passages.

Figure 2A:
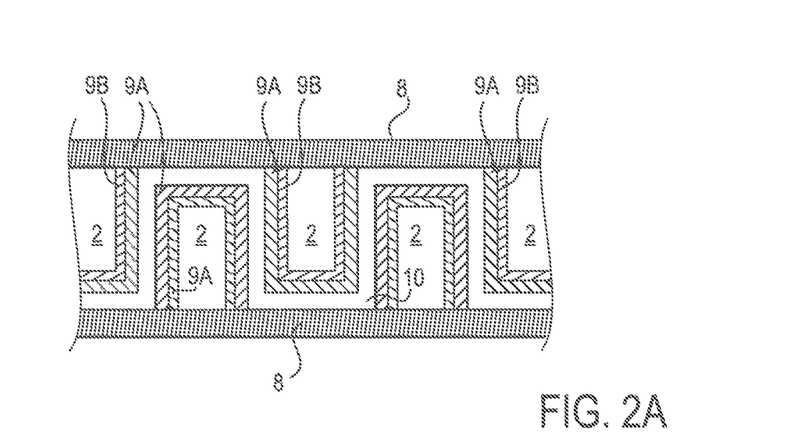
FIGS. 2A and 2B are end views of reaction passages in a compact heat exchange reactor according to another exemplary embodiment.

Alternatively, the Fischer-Tropsch component and the acidic component can be deposited on the walls of the reaction passages in separate catalyst layers. In one embodiment, as illustrated in FIG. 2A, a catalyst layer 9A of synthesis gas conversion component, also referred to as the Fischer-Tropsch layer, is deposited onto the walls 10 of the reaction passages 2, and a catalyst layer 9B of acidic component, also referred to as the zeolite layer, is deposited onto the Fischer-Tropsch layer 9A to form a coating with the FT layer inside the zeolite layer. Optional metal layer 8 can be included on either side of the reaction passages 2. Primer coating layers (not shown), e.g., layers comprising oxidic silicon nanoparticles, can be used for improving the adhesion of catalyst layers to reaction passage walls. These primer layers can be applied by CCVD processes as described in U.S. Patent Publication No. 20120198769A1.

Figure 2B:
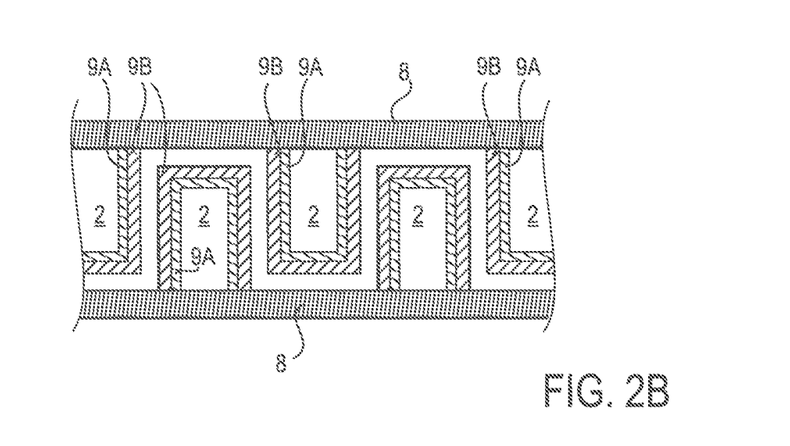

In another embodiment, as illustrated in FIG. 2B, a zeolite layer 9B is deposited onto the walls 10 of the reaction passages 2, and a Fischer-Tropsch layer 9A is deposited onto the zeolite layer 9B to form a coating with the zeolite layer inside the FT layer. The zeolite layer can contain from about 12 to about 15 g of acidic component per gram of Fischer-Tropsch metal in the Fischer-Tropsch layer.

For slurry stability, the pH of the slurry is near neutral, i.e., from about 5 to about 8. The slurry can be deposited directly onto the reaction passage walls or on silica-treated wall surfaces by any suitable means, such as by washcoating, also referred to as dip coating. Washcoating refers to a process in which the reactor body containing the passage openings, with the heat exchange passage blocked, is dipped into the slurry and removed, thereby coating the reaction passage surfaces. The reactor body support can be dipped once or multiple times to achieve a desired catalyst layer thickness or a desired catalyst amount. Between coatings, excess slurry can be removed from the reactor passages by any known means, such as by centrifugation, blowing with air, vacuum or the like, and the coated passages can be dried and or calcined at temperatures between 80° C. and 400° C. Alternatively, the slurry can be deposited onto the reaction passage wall surfaces by spraying, vapor deposition, impregnation or the like.

The thickness of the catalyst layers deposited on the reaction passage wall surfaces can vary from about 50 to about 300 μm, and can be tuned to optimize the effects of the catalyst layer thickness. The thickness of the catalyst layers will in part determine the catalytic activity in the reaction. The thicker the catalyst layer, the more important diffusion effects will be in determining specific activity and selectivity. Additionally, if the catalyst layer is sufficiently thick to impede flow through the reaction passages, pressure drop in the reactor may become excessively high. Pressure drop will be determined by the channel dimensions. For these reasons, smaller catalyst layer thicknesses may be preferred. However, smaller catalyst layer thicknesses also correspond to lower catalyst loading per unit volume and lower volumetric activities. In general, after the catalyst layers have been deposited, it has been found to be desirable to have a passage opening of at least about 300 μm.

In one embodiment of a compact heat exchange reactor, the hybrid Fischer-Tropsch catalyst optionally contains an interfacial layer between layers, such as deposited between the reaction passage wall surfaces and the innermost catalyst layer, or between multiple catalyst layers, to aid in adhesion of adjacent layers. Similarly, during preparation, the surface of each layer of the hybrid Fischer-Tropsch monolith catalyst can optionally be subjected to a modification to create a rough surface thereby improving the adhesion of subsequently applied, adjacent layers.

Figure 3:
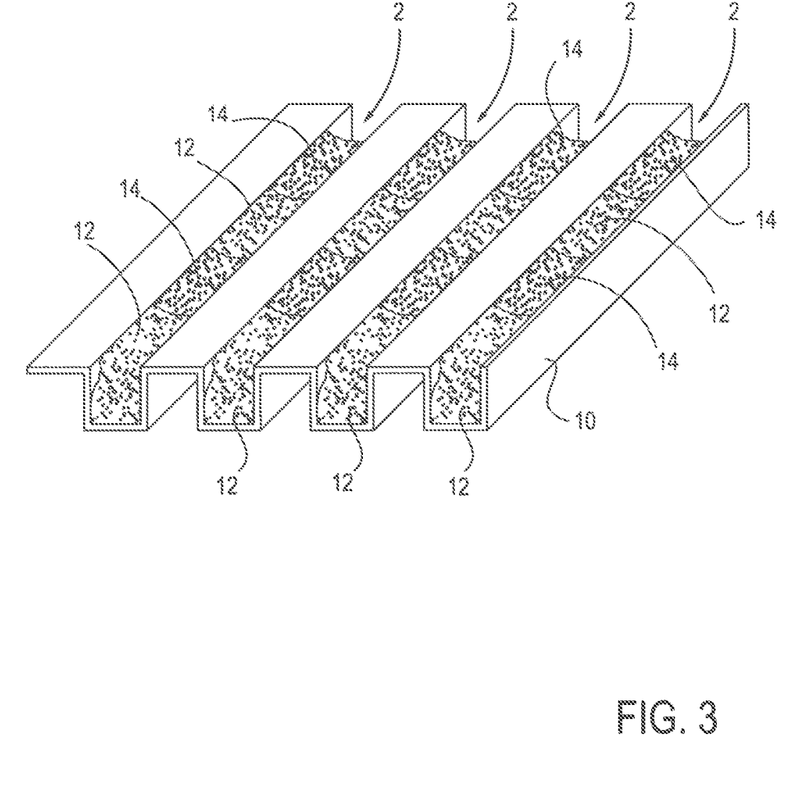
FIG. 3 is a perspective view of a set of reaction passages according to another exemplary embodiment.

In one embodiment of a compact heat exchange reactor, a Fischer-Tropsch catalyst can be prepared with a Fischer-Tropsch component in the catalyst layer deposited on the reaction passage walls without the acidic component. A reactor system can be loaded with at least one compact heat exchange reactor body containing a Fischer-Tropsch catalyst in an alternating arrangement with at least one compact heat exchange reactor body containing a zeolite catalyst. Referring to FIG. 3, a set of reaction passages 2 formed by corrugated sheet metal 10 is provided with alternating sections of Fischer-Tropsch catalyst 12 and zeolite catalyst 14. The number of alternating sections shown is for illustration only; the number can vary. In this embodiment, a synthesis gas feed of hydrogen and carbon monoxide having a $H_2/CO$ ratio from about 1.3 to about 2.0 can be contacted with the Fischer-Tropsch catalyst 12 in alternating arrangement with the zeolite catalyst 14 at a temperature from about 200° C. to about 260° C., even from about 225° C. to about 260° C., a pressure from about 5 to about 40 atmospheres, and a gaseous hourly space velocity less than 20,000 volumes of gas per volume of catalyst per hour. The resulting hydrocarbon product can contain at least 50 wt % $C_{5+}$ hydrocarbons. For stability of the zeolite catalysts, a hydrogenating metal such as Pd, Pt, or Cu may be added.

Process Conditions

The synthesis gas feed can be derived from any organic or carbon-containing material that can be gasified, including biomass, coal, shale gas, natural gas, landfill gas, solid wastes, and mixtures thereof. When the syngas feed is derived from natural gas, the $H_2/CO$ ratio in the syngas is adjusted to 1.8-2.2 by adjusting the exit temperature from the reformer. When it is derived from biomass and/or coal sources, the low $H_2/CO$ ratio of manufactured syngas should be adjusted to the 1.8-2.2 ratio by means of a water-gas-shift catalyst.

In one embodiment, the synthesis gas conversion process is conducted in the compact heat exchanger reactor at a temperature from 200 to 280° C., a pressure from 5 to 40 atmospheres, a recycle ratio from 1 to 3, and a gaseous hourly space velocity less than 20,000 volumes of gas per volume of catalyst per hour. Recycle ratio is defined as the ratio of fresh syngas feed to tail gas returned from the products footer to the feed.

Hydrocarbon Product

In one embodiment, the resulting effluent includes a hydrocarbon product containing at least 50 wt % $C_{5+}$ hydrocarbons, even at least 65 wt % $C_{5+}$ hydrocarbons, at a $C_{5+}$ productivity from 0.05 to 2 $g_{C5+}/g_{cat}/h$.

In one embodiment, the effluent produced includes a hydrocarbon product containing less than 25 wt % $C_{21+}$ hydrocarbons, even from 3 to 23 wt % $C_{21+}$ hydrocarbons. Furthermore, the pour point of the hydrocarbon product is from −10° C. to 30° C. when measured according to test method ASTM D97-11 Standard Test Method for Pour Point of Petroleum Products, published July 2011. Therefore at room temperature the hydrocarbon product is a pourable liquid, and the product is fully blendable with crude oil at or above room temperature. Crude oil can be classified as light, medium or heavy, according to its measured API gravity. For example, light crude oil can be defined as having an API gravity higher than 31.1° (less than 870 kg/m$^3$). Medium crude oil can be defined as having an API gravity between 22.3° and 31.1° (870 to 920 kg/m$^3$). Heavy crude oil can be defined as having an API gravity below 22.3° (920 to 1000 kg/m$^3$). Extra heavy crude oil can be defined as having an API gravity below 10.0° (greater than 1000 kg/m$^3$). By "fully blendable with crude oil at or above room temperature" is meant that the product can be blended with any crude oil at a temperature of 20° C. or higher such that the resulting blend has a single phase.

Compact heat exchange reactors using hybrid Fischer-Tropsch catalysts as described herein have advantages over the use of fixed bed reactors using hybrid Fischer-Tropsch catalysts in pellet, granular or extruded form. For one, heat from the exothermic Fischer-Tropsch reaction can be more readily removed, depending on the geometry of the reactor passages as well as the passage wall material. In particular, metallic materials which allow exchange of gases and vapors between innermost and outermost passages allow heat to be readily removed. Another advantage is lower production of methane by compact heat exchange reactors using hybrid Fischer-Tropsch catalysts as described herein. Without wishing to be bound by theory, it is believed that the lower production of methane is a result of the smaller particle size used in the catalyst layers in the hybrid Fischer-Tropsch catalysts as described herein with their significantly shorter diffusion paths than fixed bed catalysts in pellet, granular or extruded form. The average layer thickness of the deposited hybrid Fischer-Tropsch or conventional Fischer-Tropsch catalyst in a compact heat exchange reactor can be less than about 300 μm in diameter. Compared to an extrudate particle having a diameter of at least 1 mm, the diffusion path in the monolith catalysts should be much shorter which means less diffusion resistance difference between CO and the smaller $H_2$ which should result, in theory, in lower methane. CO hydrogenation is a function of $H_2$ concentration so when $H_2$/CO ratio is much greater than 2, as might be the case in the interior of a large particle, these conditions favor methane formation. Conventional forms of hybrid Fischer-Tropsch catalysts for fixed bed operations have a higher selectivity to methane due to higher concentration of hydrogen inside the catalyst particles. Note that, as is known to those skilled in the art, the formation mechanism for methane is partly independent of Fischer-Tropsch synthesis.

EXAMPLES

Comparative Example

A 20 weight % Co/0.15 weight % Pt/0.3 weight % Pd catalyst on a 55 weight % ZSM-12/25 weight % $SiO_2$/20 weight % $Al_2O_3$ support was synthesized as follows. First, the hybrid support was prepared using the following procedure. A $SiO_2$ support (obtained from Sigma-Aldrich, St. Louis, Mo.) was modified with 3% Zr by impregnation. Zirconium (IV) oxynitrate hydrate $ZrO(NO_3)_2.6H_2O$ (obtained from Sigma-Aldrich, St. Louis, Mo.) was used as the Zr precursor. The modified support was dried for 2 hrs at 120° C. and calcined in air for 2 hrs at 500° C. ZSM-12 zeolite powder having a Si/Al ratio of 45 (obtained from Zeolyst International, Conshohocken, Pa.), the modified silica support prepared above, and 20 wt % catapal B alumina binder (obtained from Sasol Chemicals North America LLC, Houston, Tex.) were added to a mixer and mixed for 15 minutes, resulting in a mixture having 55 wt % ZSM-12, 25 wt % $SiO_2$ and 20 wt % $Al_2O_3$. Deionized water and a small amount of nitric acid were added to the mixed powder and the mixture was mixed for 15 minutes. The mixture was then transferred to a 1 inch (2.54 cm) Bonnot BB Gun extruder and extruded using a 1/16" (0.16 cm) dieplate containing 36 holes. The extrudate was dried first at 120° C. for 2 hours and then finally calcined in flowing air at 600° C. for 2 hours.

A synthesis gas conversion catalyst containing 20 wt % Co, 0.15 wt % Pt and 0.3 wt % Pd on the 1/16 inch (0.16 cm) hybrid support extrudates was prepared in a multi-step using aqueous impregnation. Cobalt(II) nitrate hexahydrate (obtained from Sigma-Aldrich), tetraammineplatinum(II) nitrate and tetraamminepalladium(II) nitrate (obtained from Alfa Aesar) were dissolved in water. The solution was then added to dry hybrid support extrudates. The solvent was removed in a rotary evaporator under vacuum by heating slowly to 60° C. The vacuum-dried material was then further dried in air in an oven at 120° C. overnight. The dried catalyst was then calcined at 300° C. for 2 hours in a muffle furnace. The catalysts were then crushed to a particle size of 100 to 200 μm. The properties of the catalyst are shown in Table 1.

TABLE 1

| Catalyst Composition | Catalyst Particle Size, μm | BET Surface Area, $m^2$/g | Dispersion, % | Average Co Particle Diameter, nm |
|---|---|---|---|---|
| 20Co/0.15Pt/0.3Pd on 55ZSM-12/ 25$SiO_2$/20$Al_2O_3$ hybrid support | 100-200 | 149 | 8.9 | 11.1 |

Ten grams of the catalyst prepared as described above was charged to a glass tube reactor. The reactor was placed in a muffle furnace with upward gas flow. The tube was purged first with nitrogen gas at ambient temperature, after which time the gas feed was changed to pure hydrogen with a flow rate of 750 sccm. The temperature to the reactor was increased to 350° C. at a rate of 1° C./minute and then held at that temperature for six hours. After this time, the gas feed was switched to nitrogen to purge the system and the unit was then cooled to ambient temperature. Then a gas mixture of 1 volume % $O_2$/$N_2$ was passed up through the catalyst bed at 750 sccm for 10 hours to passivate the catalyst. No heating was applied, but the oxygen chemisorption and partial oxidation exotherm caused a momentary temperature rise. After 10 hours, the gas feed was changed to pure air, the flow rate was lowered to 200 sccm and the temperature was raised to 300° C. at a rate of 1° C./minute and then kept at 300° C. for two hours. At this point, the catalyst was cooled to ambient temperature and discharged from the glass tube reactor. It was transferred to a 316-SS tube reactor of 0.51 in (1.3 cm) I.D. and placed in a clam-shell furnace. The catalyst bed was flushed with a downward flow of helium for a period of two hours, after which time the gas feed was switched to pure hydrogen at a flow rate of 500 sccm. The temperature was slowly raised to 120° C. at a temperature interval of 1° C./minute, held there for a period of one hour, then raised to 250° C. at a temperature interval of 1° C./minute and held at that temperature for 10 hours. After this time, the catalyst bed was cooled to 180° C. while remaining under a flow of pure hydrogen gas. All flows were directed downward.

The catalyst prepared as described above was subjected to a synthesis run in which the catalyst was contacted with syngas containing hydrogen and carbon monoxide. Experimental conditions and results are given in Table 1.

Example

A FinTec® compact heat exchange reactor (available from Chart Energy & Chemicals, Inc., The Woodlands, Tex.), comparable to a plate fin heat exchanger, was used to conduct syngas conversion using the hybrid catalyst in the integral catalyst form. Coolant and reaction passages formed from folded, corrugated fins were brazed into the compact heat exchange reactor structure. The compact heat exchange reactor was constructed of stainless steel.

The cobalt integral Fischer Tropsch catalyst described above (Comparative Example) was loaded into the reaction passages of the compact heat exchanger reactor. A 600 hour time-on-stream performance test was conducted in the compact heat exchanger reactor unit. The test was performed in a fully automated testing rig controlled using a LabVIEW software system (available from National Instruments Corporation). The apparatus includes a lab scale compact heat exchanger unit, oil heating and cooling media system, gas feed and gas and liquid products sampling and collections systems. Temperature, pressure and gas flow rates were continuously monitored throughout the test to insure the accurate control of the system. Additionally, tail gas samples were sampled online daily using an Agilent 3000 Micro GC (available from Agilent Technologies Inc.) and liquid products were collected daily in traps at 120° C. and 0° C.

The catalyst prepared as described above was subjected to synthesis runs in which the catalyst was contacted with syngas containing hydrogen and carbon monoxide. Experimental conditions and results are given in Table 2. The results indicate that the compact heat exchanger reactor provided improved productivity when compared with the Comparative Example.

TABLE 2

|  | Comp. Ex. | | | | Example | | | |
|---|---|---|---|---|---|---|---|---|
| TOS, h | 166 | 24 | 72 | 168 | 192 | 420 | 552 | 576 |
| Temperature, ° C. | 240.0 | 201.0 | 221.0 | 233.9 | 240.0 | 250.0 | 250.0 | 250.0 |
| Pressure, atm | 20 | 20 | 20 | 20 | 20 | 20 | 20 | 20 |
| SV, mL/g/h | 13100 | 13500 | 13500 | 13500 | 13500 | 13500 | 13500 | 13500 |
| $H_2$/CO Fresh Feed | 2.00 | 2.00 | 2.00 | 2.00 | 2.00 | 2.00 | 2.20 | 2.40 |
| $H_2$ Conversion, % | 54.4 | 7.3 | 28.9 | 51.7 | 63.7 | 77.8 | 71.1 | 72.0 |
| CO Conversion, % | 51.8 | 10.0 | 26.8 | 46.7 | 53.9 | 65.7 | 65.9 | 72.5 |
| Rate, $g_{C_{5+}}$/g/h | 1.06 | 0.20 | 0.62 | 1.01 | 1.18 | 1.33 | 1.21 | 1.22 |
| Volumetric Productivity, g/h/cc | 0.05 | 0.04 | 0.17 | 0.31 | 0.40 | 0.39 | 0.40 | 0.39 |
| % $CH_4$ | 13.5 | 14.1 | 9.8 | 13.7 | 13.4 | 16.8 | 18.1 | 20.1 |
| % $C_2$ | 1.5 | 2.5 | 1.3 | 1.3 | 1.3 | 1.7 | 1.9 | 2.1 |
| % $C_3$ | 4.1 | 6.3 | 3.6 | 2.4 | 2.0 | 4.7 | 5.4 | 5.6 |
| % $C_4$ | 4.5 | 3.8 | 2.5 | 4.6 | 4.2 | 3.1 | 3.6 | 3.2 |
| % $C_{5+}$ | 74.8 | 72.0 | 82.7 | 77.1 | 78.1 | 71.9 | 69.5 | 67.6 |
| % $CO_2$ | 1.50 | 1.31 | 0.28 | 0.95 | 1.05 | 1.76 | 1.41 | 1.51 |
| $C_{5+}$ yield (g/g/h) | 0.9 | 0.1 | 0.5 | 0.9 | 1.2 | 1.1 | 1.2 | 1.1 |
| $C_{21+}$ hydrocarbons yield (g/g/h) | 0.1 | 0.0 | 0.1 | 0.2 | 0.3 | 0.1 | 0.1 | 0.1 |
| % $C_{21+}$ hydrocarbons | 15.0 | 3.6 | 18.7 | 19.8 | 22.1 | 13.2 | 6.9 | 5.2 |

The pour point of the liquid produced in Example 1 is 28° C., as measured according to test method ASTM D97-11 Standard Test Method for Pour Point of Petroleum Products, published July 2011; therefore at room temperature the liquid is pourable.

Unless otherwise specified, the recitation of a genus of elements, materials or other components, from which an individual component or mixture of components can be selected, is intended to include all possible sub-generic combinations of the listed components and mixtures thereof. Also, "comprise," "include" and its variants, are intended to be non-limiting, such that recitation of items in a list is not to the exclusion of other like items that may also be useful in the materials, compositions, methods and systems of this invention.

From the above description, those skilled in the art will perceive improvements, changes and modifications, which are intended to be covered by the appended claims.

What is claimed is:

1. A process for synthesis gas conversion comprising:
   contacting a synthesis gas feed comprising hydrogen and carbon monoxide having a $H_2$/CO ratio from 0.5 to 3.0 with a hybrid catalyst comprising particles having a particle size from 50 to 500 μm and comprising at least one zeolite and a Fischer-Tropsch component wherein the ratio of zeolite to Fischer-Tropsch component is from 0.1:1 to 30:1 and the hybrid catalyst comprises from 0.5 to 40 wt % Fischer-Tropsch component;
   in a compact heat exchange reactor comprising a set of reaction passages disposed between a synthesis gas feed header and a products header; and a set of coolant passages disposed between a coolant inlet header and a coolant outlet header; wherein the set of coolant passages conducts a coolant therethrough; and wherein the set of reaction passages conducts synthesis gas and reaction products therethrough and contains the hybrid catalyst therein;
   at a temperature from 200° C. to 280° C., a pressure from 5 to 40 atmospheres, a recycle ratio from 1 to 3, and a gaseous hourly space velocity less than 20,000 volumes of gas per volume of catalyst per hour;
   to produce an effluent including a hydrocarbon product containing at least 50 wt % $C_{5+}$ hydrocarbons and less than 5 wt % $C_{21+}$ hydrocarbons at a $C_{5+}$ productivity from 0.05 to 2 $g_{C5+}/g_{cat}$/h.

2. The process of claim 1 wherein the Fischer-Tropsch component comprises cobalt and the ratio of zeolite to Fischer-Tropsch component is from 1:1 to 15:1 and the hybrid catalyst comprises from 5 to 45 wt % Fischer-Tropsch component.

3. The process of claim 1 wherein the hybrid catalyst comprises a support comprising at least one zeolite and a Fischer-Tropsch component comprising cobalt deposited on the support.

4. The process of claim 1 wherein the hybrid catalyst comprises an intimate mixture of at least one zeolite and a Fischer-Tropsch component comprising cobalt.

5. The process of claim 1 wherein the hybrid catalyst particles have a particle size from 75 to 300 μm.

6. The process of claim 1 wherein the hybrid catalyst comprises from 15 to 40 wt % Fischer-Tropsch component.

7. The process of claim 1 wherein the effluent produced includes a hydrocarbon product containing at least 65 wt % $C_{5+}$ hydrocarbons.

8. The process of claim 1 wherein the effluent produced includes a hydrocarbon product containing less than 25 wt % $C_{21+}$ hydrocarbons.

9. The process of claim 1 wherein the effluent produced includes a hydrocarbon product containing less than 6 wt % $C_{21+}$ hydrocarbons.

10. The process of claim 1 wherein the temperature is from 220° C. to 240° C. and the pressure is from 10 to 25 atmospheres.

11. The process of claim 1 wherein the effluent produced includes a hydrocarbon product having a pour point of from −10° C. to 30° C.

12. The process of claim 1 wherein the effluent produced includes a hydrocarbon product fully blendable with crude oil at or above room temperature.

13. The process of claim 1 wherein the synthesis gas feed is derived from natural gas and has a $H_2/CO$ ratio from 1.8 to 2.2 and the Fischer-Tropsch component comprises cobalt.

14. The process of claim 1 wherein the synthesis gas feed is derived from landfill gas and has a $H_2/CO$ ratio from 1.8 to 2.2 and the Fischer-Tropsch component comprises cobalt.

15. The process of claim 1 wherein the reaction passages have a hydraulic diameter of less than 6 mm and the coolant passages have a hydraulic diameter of less than 6 mm.

* * * * *